(12) United States Patent
Wyman et al.

(10) Patent No.: US 8,101,024 B2
(45) Date of Patent: Jan. 24, 2012

(54) REMOVAL OF MINERALS FROM CELLULOSIC BIOMASS

(75) Inventors: Charles E. Wyman, Norwich, VT (US); Todd A. Lloyd, Hartland, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 409 days.

(21) Appl. No.: 12/366,360

(22) Filed: Feb. 5, 2009

(65) Prior Publication Data
US 2009/0142848 A1 Jun. 4, 2009

Related U.S. Application Data

(62) Division of application No. 11/293,639, filed on Dec. 2, 2005, now Pat. No. 7,503,981.

(60) Provisional application No. 60/632,483, filed on Dec. 2, 2004.

(51) Int. Cl.
*C08B 37/00* (2006.01)
*C12P 19/00* (2006.01)
*C12P 19/14* (2006.01)
*D21C 3/04* (2006.01)

(52) U.S. Cl. ............... 127/37; 127/36; 16/1; 16/4; 16/7; 16/125; 435/72; 435/99; 436/79; 436/102; 436/119

(58) Field of Classification Search .................... 127/36, 127/37; 162/1, 4, 7, 125; 435/72, 99; 436/79, 436/102, 119
See application file for complete search history.

(56) References Cited

U.S. PATENT DOCUMENTS

| | | | |
|---|---|---|---|
| 4,110,281 A | 8/1978 | Dreer | |
| 5,336,325 A | 8/1994 | Devilbiss et al. | |
| 5,705,216 A | 1/1998 | Tyson | |
| 5,792,315 A | 8/1998 | Landfors et al. | |
| 6,409,841 B1 | 6/2002 | Lombard | |
| 6,555,350 B2 | 4/2003 | Ahring et al. | |
| 7,503,981 B2 * | 3/2009 | Wyman et al. .................. | 127/37 |

OTHER PUBLICATIONS

Select File History from related U.S. Appl. No. 11/293,639 dated Feb. 21, 2008 through Nov. 4, 2008, 28 pages.

* cited by examiner

*Primary Examiner* — Herbert J Lilling
(74) *Attorney, Agent, or Firm* — Lathrop & Gage LLP

(57) ABSTRACT

Disclosed is a method for removing minerals from a cellulosic biomass. For example, the biomass may be prewashed with an acid solution and rinsed with water to remove minerals prior to acid saccharification. The removal of minerals may reduce overall acid requirements, and decrease pretreatment costs.

15 Claims, 6 Drawing Sheets

REMOVAL OF MINERALS FROM CELLULOSIC BIOMASS

CROSS REFERENCE TO RELATED APPLICATION

This is a divisional application of U.S. patent application Ser. No. 11/293,639, filed Dec. 2, 2005 now U.S. Pat. No. 7,503,981 which claims priority to U.S. Provisional Patent Application No. 60/632,483, filed Dec. 2, 2004, the disclosures of which are incorporated herein by reference.

GOVERNMENT INTERESTS

The United States Government may have certain rights in the present invention as research relevant to its development was funded by the United States Department of Agriculture Initiative for Future Agricultural and Food Systems Program contract number 00-52104-9663.

BACKGROUND

1. Field of the Invention

The present invention pertains to the field of processing biomass to produce fuels, chemicals and other useful products and, more specifically, to hydrolyzing cellulosic biomass to produce sugars for conversion to ethanol and other products. Use of a prewash to remove minerals before acidifying the biomass results in significantly improved acid pretreatment efficiency.

2. Description of the Related Art

Cellulosic biomass represents an inexpensive and readily available source of sugars. These sugars may be used alone, fermented to produce alcohols and industrial chemicals, or chemically converted to other compounds. For example, cellulosic biomass is useful for generating ethanol, which has a number of industrial and fuel uses. Of particular interest is the use of ethanol as a gasoline additive that boosts octane, reduces pollution, and partially replaces gasoline in fuel mixtures.

Generally speaking, biomass, e.g., wood, grass, forest or crop residue, contains cellulose wrapped in a recalcitrant lignin and hemicellulose sheath. The sheath must be chemically and/or physically disrupted in a pretreatment step that produces some sugars and provides access to cellulose. Typical pretreatment protocols involve mechanical size reduction, acid hydrolysis, ammonia or alkali treatment, and/or steam explosion. High capital and operating costs are associated with all of these pretreatment methods. For example, most of the pretreatments are carried out at high temperatures and a considerable amount of energy is used to heat the biomass. These high temperatures create the evolution of steam and other gaseous products which create high pressures, with concomitantly high containment costs. Further, the elevated pressures make it difficult to introduce solid materials into the reactor.

In acid pretreatments, nitric or hydrochloric acid may be used, but sulfuric acid is often favored because of its lower cost. However, pretreatment expenditures may still be large when sulfuric acid is used because substantial quantities of acid are required, and neutralization and disposal costs remain. It has been found by A. Esteghlalian, A. G. Hashimoto, J. J. Fenske, and M. H. Penner, *Bioresour. Technol.*, 59, 1997, 129-136 and J. N. BeMiller, *Adv. Carbohydr. Chem.*, 22, 1967, 25-108, that cellulosic biomass can have a significant mineral content, and that these minerals neutralize some of the acid during dilute-acid pretreatment, which increases acid demand. For example, mineral oxides combine with sulfuric acid to form sulfate salts and water:

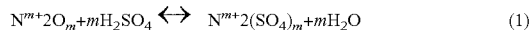

$$N^{m+}2O_m + mH_2SO_4 \leftrightarrow N^{m+}2(SO_4)_m + mH_2O \qquad (1)$$

where N is potassium, sodium, calcium, iron and other cations, and m is an integer equal to the charge of the cation. This neutralization reaction consumes hydrogen ions in the formation of water.

Specific to sulfuric acid is an equilibrium shift to formation of bisulfate that can further reduce hydrogen ion concentrations and compound the effect of neutralization, as reported by J. M Readnour and J. W. Cobble, *Inorg. Chem.*, 8(10), 1969, 2174-2182. Equation (2) shows the sulfate salt formed in Equation (1) combining with hydrogen ions to form a bisulfate salt:

$$N^{m+}2(SO_4)_m + mH^+ \leftrightarrow N^{m+}(HSO_4)_m + N^{m+} \qquad (2)$$

This equilibrium shift has a more pronounced effect at lower acid concentrations, where the quantity of hydrogen ion consumed in Equation (2) represents a large percentage of the total hydrogen ion concentration. Further, bisulfate salt formation is favored when dilute solutions are subjected to the high temperatures used for pretreatment reactions because the equilibrium constant, $K_2 = ([H^+][SO_4^{2-}])/[HSO_4^-]$, decreases as temperature increases. Due to both bisulfate salt formation and a shift in the sulfuric acid dissociation equilibrium, an increase in pH is observed and additional acid is required to achieve a particular reaction rate.

SUMMARY

The present invention advances the art and overcomes the problems outlined above by providing an improved and more efficient method for the use of acid in biomass conversion processes.

In one embodiment, a method for enhancing cellulosic saccharification includes removing minerals from a cellulosic biomass by use of an acid prewash that is substantially separated from the cellulosic biomass before acid pretreatment, to reduce the mineral content of the biomass, wherein the acid prewash contains acid in an effective amount to remove a beneficial quantity of minerals in the biomass without substantially hydrolyzing hemicellulose or cellulose in the biomass, and thereafter pretreating the biomass by the use of acid.

In one embodiment, a method for enhancing cellulosic saccharification includes removing minerals from a cellulosic biomass by use of an acid prewash that is substantially separated from the cellulosic biomass before acid pretreatment, to reduce the mineral content of the biomass, wherein the acid prewash contains acid in an effective amount to remove a beneficial quantity of minerals in the biomass without substantially hydrolyzing hemicellulose or cellulose in the biomass, and thereafter pretreating the biomass by the use of acid.

The removal of minerals from a cellulosic biomass may be followed by one or more saccharification steps. For example, acid hydrolysis may be used alone or followed by enzymatic hydrolysis.

In one embodiment, a method of evaluating the effect of mineral content in a cellulosic biomass includes determining the amount of sulfuric acid consumed by mineral neutralization and bisulfate salt formation per mass of cellulosic biomass. The method may further include determining a pH of a slurry of the cellulosic biomass and optionally comparing the pH of the slurry of the cellulosic biomass with the pH of a slurry of an ideal cellulosic biomass.

DETAILED DESCRIPTION

There will now be shown and described a method for increasing process efficiency in making useful products out of cellulosic biomass. For cellulosic substrates, efficiency is improved by treating the biomass with an acid wash followed by a water wash to remove minerals.

Figure 1:
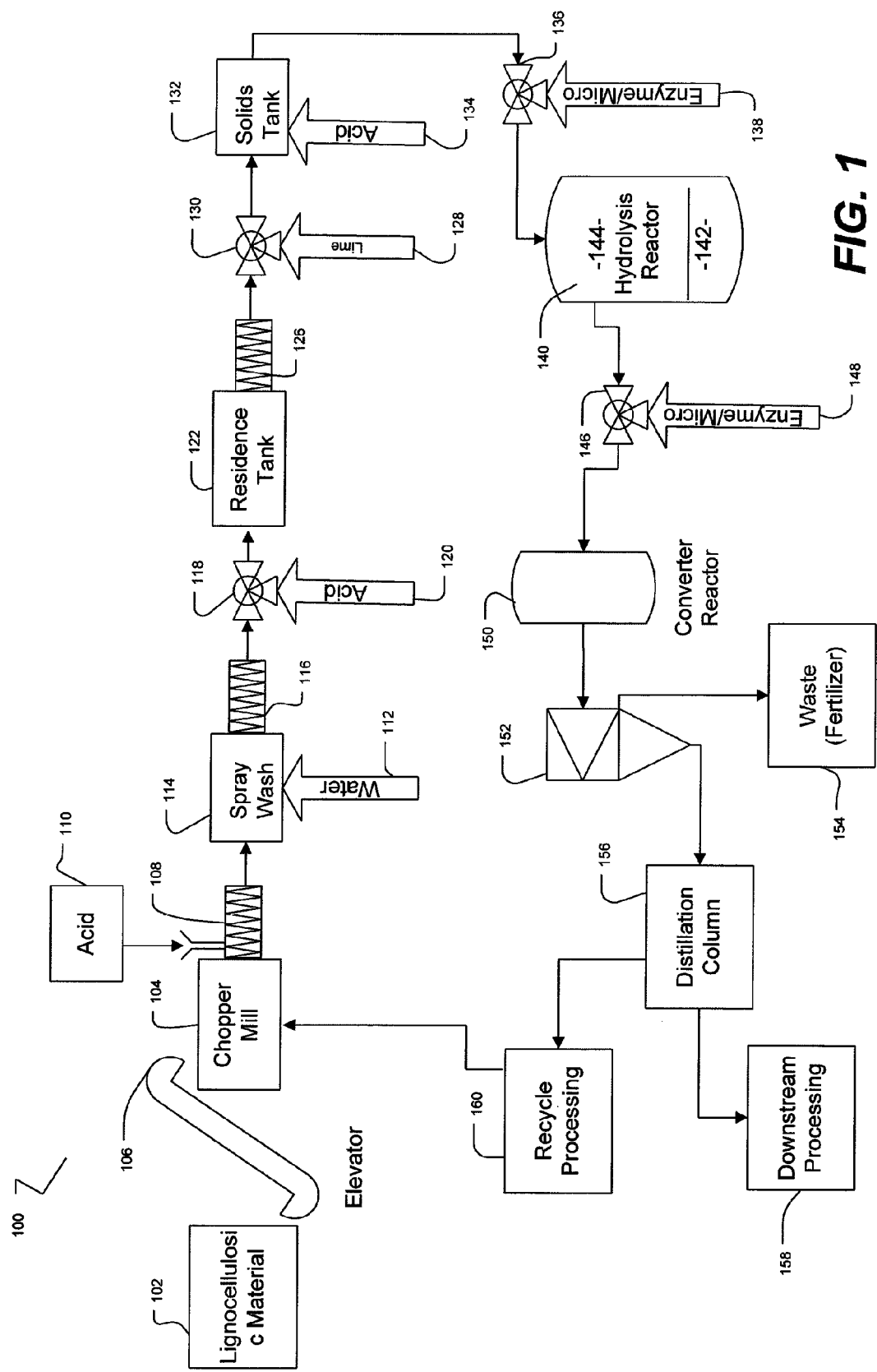
FIG. 1 is a schematic diagram showing process equipment that may be used according to one embodiment.

FIG. 1 shows one embodiment of a reactor system 100 that may be used for biomass conversion. Particulate cellulosic material 102 is conveyed to chopper mill 104 by the action of transfer device 106, such as an elevator or slurry pipeline. The chopper mill 104 chops and/or grinds the cellulosic material 102, as needed, to a predetermined size that is suitable for downstream processing. Appropriate particle sizes vary with the feedstock and its inherent physical properties, as well as the flow conditions. In most processes, particle sizes appropriate for ground wood are in the range of about 0.1 mm to 30 mm preferably in the range of 0.5 mm to 4 mm. Other materials may be larger or smaller depending on the particular materials, particularly those having at least one thin dimension such as paper or straw. If the effects of gravity or floatation are relied upon to cause movement of the solid cellulosic material with respect to the liquid, then particle size may need to be adjusted appropriately to permit solid/liquid movement. Optimum sizes depend on the particular cellulosic material used and the reactor size and construction and are readily determinable by routine empirical studies for a reactor and reactor flow conditions. Hydrolysis generally proceeds faster with a smaller particle size. An economic optimization may be reached between the costs of grinding the cellulosic material and the cost advantages of higher throughput. Smaller particle sizes inherently provide more surface area. On the other hand, for a given set of flow conditions, particles that are too small may form a dense mat, which is difficult for fluid to penetrate at an acceptable rate.

It will be appreciated that the cellulosic material may be any feedstock that contains cellulose. In various embodiments, the cellulosic biomass comprises wood, corn stover, sawdust, bark, leaves, agricultural and forestry residues, grasses such as switchgrass, ruminant digestion products, municipal wastes, paper mill effluent, newspaper, cardboard, or combinations thereof. Reactor system 100 may accept various feedstocks and any agricultural, industrial, or municipal process that uses or discharges such wastes may be modified to incorporate reactor system 100.

A screw extruder 108 transfers the chopped cellulosic material from chopper mill 104. An acid prewash 110 may be added to screw extruder 108. For example, the acid may be selected from the group consisting of hydrochloric, nitric, and sulfuric acid present at about 0.01 to 10% by weight acid, or from 0.05 to 5% by weight acid, or from 0.1 to 2% by weight acid, or from 0.1 to 1% by weight acid based on the weight of dry cellulosic material 102. The prewash step may be performed at a temperature of about 25-85° C. Preferably, the acid prewash as characterized by these concentrations removes minerals in the biomass without hydrolyzing hemicellulose or cellulose. The cellulosic material 102 may be rinsed with water 112 in spray washer 114 to remove acid prewash 110, thus creating a substantially mineral-free or reduced mineral biomass.

A "substantially mineral-free" biomass is a biomass that has been treated to remove at least a portion of the minerals present in the biomass prior to treatment. For example, at least about 1%, 2%, 3%, 4%, 5%, 10%, 20%, 25%, 30%, 40%, 50%, 60%, 70%, 75%, 80%, 85%, 90%, 95%, 97%, 98%, or 99% of the minerals present in the untreated biomass are removed. The biomass is treated, for example with an acid that will react with and solubilize the minerals. The solubilized minerals may be separated from the biomass to produce a substantially mineral-free biomass. An "ideal" cellulosic biomass is a theoretical biomass having 0% mineral content.

Spray washer 114 discharges into a screw conveyor 116, which at a first three way mixing station 118 mixes the substantially mineral-free biomass with an acidification solution 120 that contains, for example, from 1% to 5% by weight of a dilute sulfuric acid solution. The acidified slurry may be transferred to a residence tank 122.

The slurry exits residence tank 122 into a second screw conveyor 128, which at a second three way mixing station 130 mixes the slurry with a lime solution 128, e.g., one with sufficient lime to impart a predetermined pH of 10 to 11. The slurry is discharged into a solids holding tank 132 where it resides for an appropriate time permitting the lime to remove deleterious byproducts of acid hydrolysis. Additional acid 134, such as sulfuric acid, may be added into the solids holding tank 132 to adjust pH into a range from 5 to 7. The solids holding tank 132 discharges into a third three way mixing station 136.

In turn, the third three way mixing station 136 introduces an enzymatic solution 138 that contains a hydrolyzing enzyme, for example, cellulase or a mixture of cellulase and other enzymes including beta-glucosidase. Alternatively, the enzymatic solution 138 contains an inoculum and growth medium including a microorganism capable of saccharifying the slurry by the in vivo production of enzymes. The slurry travels to a heated hydrolysis reactor vessel 140, which may be one of a series of such reactor vessels, for an appropriate residence time permitting hydrolysis of the slurry. For example, this residence time may be from one to three days. A series (not shown) of hydrolysis reactor vessels 140 may permit continuous batch processing. The hydrolysis reactor 140 may, for example, be a flow-through reactor in which solids 142 are retained for an interval of time with recycle of fluids 144, a fluidized bed reactor with fluid recycle, or a stir-tank.

By way of example, use of a continuous stirred tank enzymatic hydrolysis reactor, or a series of such reactors, has been shown to produce substantially equivalent saccharification results to the use of a batch reactor that is essentially a residence tank. The downstream reactors may be other stirred reactors, batch reactors or plug flow reactors (not shown in FIG. 1).

Slurry discharge from hydrolysis reactor 140 may be subjected to additional mixing at a fourth mixing station 146, which adds a second solution 148, such as a microorganism-containing solution for conversion of sugars into ethanol. The second solution 148 reacts in a converter reactor 150, for example, to convert sugars into alcohol or other organic compounds. Discharge from converter reactor 150 may be submitted to a distillation column 156, which concentrates useful products, e.g., ethanol, for further downstream processing 158, such as by a molecular filter to remove water. Nonvolatile solvents and solids from distillation column 156 are charged into a vortex separator 152, which discharges solids to waste disposal 154 where the solids may, for example, be used as a boiler fuel. Liquids from vortex separator 152 are submitted to recycle processing 160, for example, to filter fine particulates.

It will be appreciated that the equipment shown generally in FIG. 1 may be used or adapted to implement a variety of known processes. The prior processes do not include use of a prewash composition, such as acid prewash 110, and may be adapted for such use according to the instrumentalities described herein. The aforementioned use of the prewashing composition 110, results in significant cost reductions in the overall process of producing sugars or fermented organic compounds from cellulose by reducing the amount of acid necessary for pretreatment.

Generally, any cellulosic acid saccharification process may be improved by removing minerals from the biomass prior to saccharification. The process may, for example, entail making pulp, making paper, treating effluent from a pulp manufacturing process, treating effluent from a process of making paper, a bioconversion process, a biopolymer process, a waste treatment process, and combinations thereof.

Among the processes for producing ethanol from cellulosic substrates are those known as the Direct Microbial Conversion (DMC) process and the Simultaneous Saccharification and Fermentation (SSF) process. These processes can use a variety of microorganisms to convert organic material to ethanol. In the DMC method, a single microbial system both produces cellulase enzyme and produces ethanol as a fermentation product. The SSF method utilizes two biological elements, one that is based on cellulase enzyme and the other using one or more microorganisms to ferment sugars to ethanol or other products.

As an alternative to adding cellulase in enzymatic solution 138, cellulase may be produced using a biomass fermentation process, for example, in a DMC process as described in Brooks et. al., *Proc. Annu. Fuels Biomass Symp.*, 2$^{nd}$ (1978), or an SSF process as described in Ghose et. al., *Biotechnol. Bioeng.*, 26 (4): 377-381 (1984). These processes may be used, as modified by the use of acid prewashing, according to the principles described herein. One example of an organism that is useful in converting organic matter to ethanol by way of the DMC process is *Clostridium thermocellum*. Other examples of suitable microorganisms that may be used with the DMC process option include *Fusarium oxysporum* and *C. cellulolyticum*. In addition, such organisms can be used in co-culture with *C. thermosaccharolyticum* or similar pentose-utilizing organisms such as *C. thermohydrosulfuricum* and *Thermoanaerobacter ethanoliticus*. An example of another microorganism that may be used in practice according to the SSF process is *Sacchararomyces cerevisiae* (which produces ethanol).

A variety of suitable growth media for microbial digestion processes are well known in the art. Generally, a suitable growth medium is able to provide the chemical components necessary to maintain metabolic activity and to allow cell growth.

As shown in FIG. 1, pH is altered by the lime solution 128, which may also occur downstream of positions shown in FIG. 1. Any of the known cellulases, cellulase complexes, or other cellulose hydrolyzing enzymes, may be used in the enzymatic solution 138. Further, a lignin-blocking polypeptide may optionally be added before, during or after addition of cellulase. A lignin-blocking polypeptide will generally reduce the amount of cellulase required to achieve a desired conversion efficiency. Exemplary lignin-blocking polypeptides include bovine serum albumin, soybean protein, amylase, whey protein, and combinations thereof. Cellulase digestion may be performed, for example, for one to three days at a temperature that is optimal for the cellulase to produce a sugar-containing solution. The sugar-containing solution is then separated from the residues, for example, by filtration, sedimentation, or centrifugation. The sugar-containing solution may be processed to recover sugar or further reacted or fermented to produce a desired organic chemical, such as an alcohol.

In some embodiments, the reactor vessels 140 and 150 generally may have a solids content of about 5% to 50%, preferably 8% to 50%, when the solids are present with the liquid at the end of the hydrolysis. The higher solids content is generally more desirable but the concentration may be limited by reactor design and the need for fluid to heat the solids.

Cellulose digestion primarily produces glucose in hydrolysis reactor 140. A variety of microorganisms may be used to produce an even wider assortment of organic compounds in the converter reactor 150. The residue digest may be fermented in any manner known per se to utilize glucose.

As an alternative to separate cellulase digestion and fermentation, both reactions may occur concomitantly in simultaneous saccharification and fermentation processes, for example, within hydrolysis reactor 140. Any fermentation that is operable in conditions suitable for cellulase is acceptable. The conditions and concentrations in simultaneous saccharification and fermentation (pH, temperature, etc.) may be measured and adjusted to be optimized for either saccharification or fermentation or for overall optimization. The conditions may be changed as the process progresses.

Example 1

Mathematical Model

Mathematical concepts that, generally, provide a theoretical basis showing that acid pretreatment is beneficially impacted by prewashing the biomass to remove minerals are described below.

Hemicellulose hydrolysis is assumed to be a first-order homogenous reaction in hemicellulose, where acid catalyzes the conversion of polymeric hemicellulose, HE, into 5-carbon xylose units, X, $$HE + H_3O^+ \xrightarrow{k_h} X + H_3O^+ \quad (3)$$

The rate constant is:

$$k_h = Ae^{-E/RT} \quad (4)$$

in which the preexponential factor, A, is a function of acid concentration, but the activation energy, E, is considered independent of temperature and acid concentration. This expression can be rewritten to explicitly include the effect of acid concentration:

$$A = A_0 C^m \quad (5)$$

in which C is the acid concentration in percent added prior to hydrolysis, and m is an arbitrary constant that varies with the type of biomass being pretreated. Equations 4 and 5 can be combined to give:

$$k_n = A_0 C^m e^{-E/RT} \quad (6)$$

Typical values of m of between about 0.4 and 1.6 have been reported in the literature (Esteghlalian et al., 1997). The use of percent acid in this expression appears to be arbitrary. Other investigators have used normality or molarity of the added acid, and yet others have used the pH taken at room temperature after hydrolysis. This arbitrary use of the acid concentration may explain why the power term m and the kinetic rate constants vary so widely, even for investigations using the same substrate.

Both Equations 5 and 6 show that hydrogen ion concentration should affect the rate of hemicellulose hydrolysis, but the neutralization capacity of biomass is not taken into consideration. Neutralization is caused by basic minerals containing potassium, sodium, calcium, iron and other cations present in biomass reacting with sulfuric acid and reducing available hydrogen ions stoichiometrically (BeMiller, 1967):

$$N^{m+}2O_m + mH_2SO_4 = N^{m+}2(SO_4)_m + mH_2O \tag{1}$$

in which $N^{m+}$ is the cation and m is its valence. Mineral content varies from species to species and neutralization capacity may be determined experimentally, or correlated with mineral analyses. In a dry method described in Tappi, Ash in wood, pulp, paper and paperboard: combustion at 525° C., in document number TAPPI T-211, Technical Association of the Pulp and Paper Industry, Norcross, Ga., 2002, a biomass sample is ashed, and the ash is neutralized with an excess of sulfuric acid, which is back-titrated with sodium hydroxide to determine mineral content.

The dissociation of sulfuric acid is described by the following coupled equations:

$$H_2SO_4 \xleftrightarrow{K_1} H^+ + HSO_4^- \tag{7}$$

$$HSO_4^- \xleftrightarrow{K_2} H^+ + SO_4^{2-} \tag{8}$$

The equilibrium concentrations of each species can be predicted from the dissociation constants $K_1$ and $K_2$ as follows:

$$K_1 = \frac{[H^+][HSO_4^-]}{[SO_4^{2-}]} \tag{9}$$

$$K_2 = \frac{[H^+][SO_4^{2-}]}{[HSO_4^-]} \tag{10}$$

Where $K_1$ is large (i.e., the first dissociation reaction is essentially complete), then the total hydrogen ion concentration is primarily affected by the second dissociation reaction, and Equation 10 can be rearranged to:

$$[SO_4^{2-}] = K_2 \frac{[HSO_4^-]}{[H^+]} \tag{11}$$

When partial neutralization of added sulfuric acid occurs because of minerals in the biomass, some hydrogen ions are converted to water and some sulfate anion is associated with mineral cations (Eq. 1). The sulfate balance can be expressed as the concentration of sulfate anions from the dissociation of sulfuric acid plus the concentration of bisulfate anions from the dissociation of sulfuric acid, minus the concentration of sulfuric acid remaining after neutralization, M, minus the sulfate concentration resulting from neutralization, N:

$$[HSO_4^-] + [SO_4^{2-}] - M - N = 0 \tag{12}$$

Substituting the expression for $[SO_4^{2-}]$ from Equation 11 into Equation 12 produces:

$$[HSO_4^-] + K_2 \frac{[HSO_4^-]}{[H^+]} - M - N = 0 \tag{13}$$

The charge balance can be expressed as:

$$[H^+] + 2N - [HSO_4^-] - 2[SO_4^{2-}] = 0 \tag{14}$$

or $$[H^+] + 2N - [HSO_4^-] - 2K_2 \frac{[HSO_4^-]}{[H^+]} = 0 \tag{15}$$

Then from the sulfate balance (Eq. 13) one can obtain:

$$[HSO_4^-] = \frac{[H^+](M+N)}{[H^+] + K_2} \tag{16}$$

Substituting this result into the charge balance (Eq. 15) and eliminating $[HSO_4^-]$, the following quadratic equation results:

$$[H^+]^2 + (K_2 + M - N)[H^+] - 2K_2 M = 0 \tag{17}$$

Solving for $[H^+]$ leads to:

$$[H^+] = \frac{-(K_2 + M - N) + \sqrt{(K_2 + M - N)^2 + 8K_2 M}}{2} \tag{18}$$

A second effect on hydrogen ion activity is the formation of bisulfate that occurs with neutralization. Neutralization products are water and mineral sulfates (Eq. 1). These mineral sulfates, if not removed from the system, will form bisulfates through reaction with hydrogen ions (Eq. 2), $$N^{m+}2(SO_4)_m + mH^+ \leftrightarrow N^{m+}(HSO_4)_m + N^{m+} \tag{2}$$

Bisulfate formation further reduces the hydrogen ion concentration, and increases the solution pH.

Figure 2:
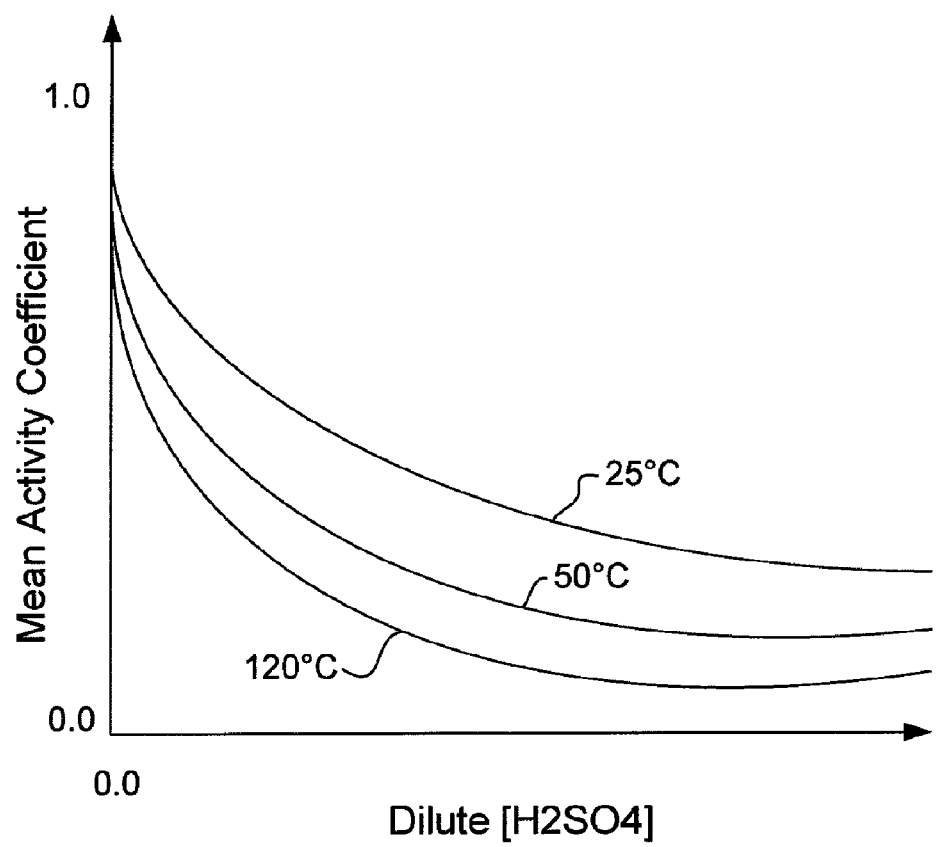
FIG. 2 is a graphical representation of mean activity coefficient versus dilute sulfuric acid concentration.

Equation 18 may be used to predict the hydrogen ion activity for dilute sulfuric acid solutions containing neutralization salts with a concentration of N mol/L at a standard temperature such as 25° C. for which dissociation constants have been tabulated. However, modifications are required to predict the hydrogen ion activity at elevated temperatures of about 100° C. to >200° C., typical for hemicellulose hydrolysis. Increasing temperature generally accelerates rates due to an increased frequency of molecular collisions, but temperature also affects the activity of hydrogen ions. The activity, or effective ion concentration, takes into account solution non-idealities, such as the effective hydrated radii of the charged species and solution expansion. Although a pH meter measures hydrogen ion activity, it is difficult if not impossible to measure pH reliably above about 100° C., and hydrogen ion activity generally must be estimated for higher temperatures. In this case, the solution dissociation constant $K_2$ in Equation 18 is related to the thermodynamic dissociation constant $K_2^0$, the solution dissociation constant extrapolated to infinite dilution, by:

$$K_2^0 = \frac{a_{H^+} a_{SO_4^{2-}}}{a_{HSO_4^-}} = \frac{[H^+][SO_4^{2-}]}{[HSO_4^-]} \frac{\gamma_{H^+} \gamma_{SO_4^{2-}}}{\gamma_{HSO_4^-}} = K_2 \frac{\gamma_{H^+} \gamma_{SO_4^{2-}}}{\gamma_{HSO_4^-}} \tag{19}$$

$$K_2 = K_2^0 \frac{\gamma_{H^+} \gamma_{SO_4^{2-}}}{\gamma_{HSO_4^-}} \tag{20}$$

in which $\alpha_i$ is the ionic activity (mol/L), and $\gamma_i$ is the ionic activity coefficient. FIG. 2 is a graphical representation of mean activity coefficient versus dilute sulfuric acid concentration. Ideal behavior is observed at infinitely dilute concentrations when the mean activity coefficient approaches 1.0, and $K_2=K_2^0$. For a constant temperature, a decrease in acid concentration relates to an increase in activity; therefore, the pH of a solution may not be affected linearly by a doubling or halving, for example, of the acid concentration. Further, for dilute sulfuric acid solutions, activity decreases as temperature increases, and pH becomes increasingly temperature dependent as concentration decreases.

The relation developed by W. L. Marshall and E. V. Jones, J. Phys. Chem., 70/12, 1966, 4028-4040, from experiments determining the solubility of calcium sulfate in sulfuric acid solutions at elevated temperatures can be used to estimate the values of the thermodynamic dissociation constant, $K_2^0$, as a function of temperature:

$$\text{Log } K_2^0 = 56.889 - 19.8858 \text{ Log } T - 2307.9/T - 0.006473T \quad (21)$$

in which T is the temperature in Kelvin. For the activity coefficients, γi, an empirical correlation by C. W. Davies, "The Conductivity of Solutions and the Modern Dissociation Theory", J. Wiley & Sons: New York, N.Y., 1930, which is a modification of the Debye-Hückel limiting law may be used:

$$-\text{Log}\gamma_i = Az^2\left(\frac{\sqrt{I}}{1+\sqrt{I}} - 0.2I\right) \quad (22)$$

in which I is the ionic strength, $$\frac{1}{2}\sum n_i z_i^2;$$

$\gamma_i$ is the ionic activity coefficient; A is the Debye-Hückel constant=$1.825\times10^6(\epsilon T)^{-1.5}$; $\epsilon$ is the dielectric constant of water=$132.88-0.208T$; z is the ionic charge; n is the ion molarity; and T is the temperature in Kelvin. Assuming that the two monovalent activity coefficients are equal, the expression for the solution dissociation constant after rearranging Equation 20 becomes:

$$K_2 = \frac{K_2^0}{\gamma_{SO_4^{2-}}} \quad (23)$$

Substituting this result into Equation 18, with the activity of the hydrogen ion $\alpha_{H+}=[H^+]\gamma_{H+}$ in which $\alpha_{H+}$ is in mol/L) produces:

$$a_{H^+} = \quad (24)$$
$$\left\{-\left(\frac{K_2^0}{\gamma_{SO_4^{2-}}} + M - N\right) + \left[\left(\frac{K_2^0}{\gamma_{SO_4^{2-}}} + M - N\right)^2 + 8\frac{K_2^0}{\gamma_{SO_4^{2-}}}M\right]^{1/2}\right\}\frac{\gamma_{H^+}}{2}$$

This expression predicts the hydrogen ion activity for any concentration of neutralization products and at any temperature. By inserting hydrogen ion activity in the kinetic rate expression of Equation 6 in place of the acid term, one obtains:

$$k_h = A_0 \alpha_{H^+} e^{-E/RT} \quad (25)$$

To make Equation 25 dimensionally consistent with Equation 6, one can convert $\alpha_{H+}$ to mole fraction from molarity by dividing by the overall mole density of solution (also a function of temperature). An expression that includes the effect of temperature and neutralization on added acid, and that can be used to predict pretreatment hydrolysis performance is obtained.

Example 2

Figure 3:
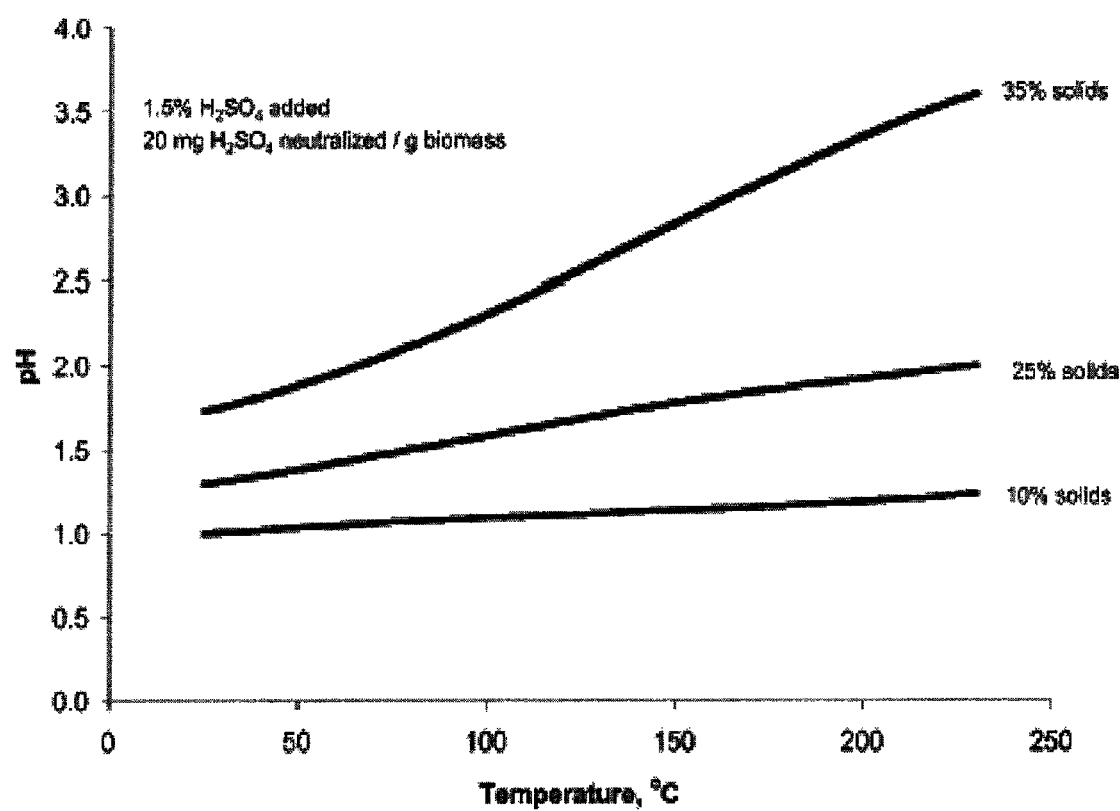
FIG. 3 shows calculated temperature versus pH curves at various solid loadings.

Analysis of Neutralization, Bisulfate Formation and Temperature on Hemicellulose Hydrolysis Several different concentrations of biomass solids are added to a 1.5% $H_2SO_4$ solution and treated over a temperature range of 25-160° C. It is known that 20 mg of sulfuric acid is neutralized per g of dry biomass, and pH, defined as $pH=-\text{Log}_{10}\alpha_{H+}$ is taken as the measure of hydrogen ion concentration. FIG. 3 illustrates how pH varies with temperature based on Equation 25 at 10, 25 and 35% solids concentration, and hence three different neutralization product (sulfate salt) concentrations. A sharp rise in pH with increasing temperature in the presence of neutralization products occurs owing to formation of bisulfate ion via Equation 2 and the impact of temperature on hydrogen ion activity via Equation 25. The pH rises about 0.15 units for a solids loading of 10% and about 1.2 units for a solids loading of 35%, corresponding to about a 29 and a 94% reduction in hydrogen ion activity, respectively. By contrast, if there had been no neutralization, the pH would rise just 0.11 units, from 0.89 to 1.00, over the same temperature range, regardless of solids loading, corresponding to a 22% reduction in hydrogen ion activity.

Figure 4:
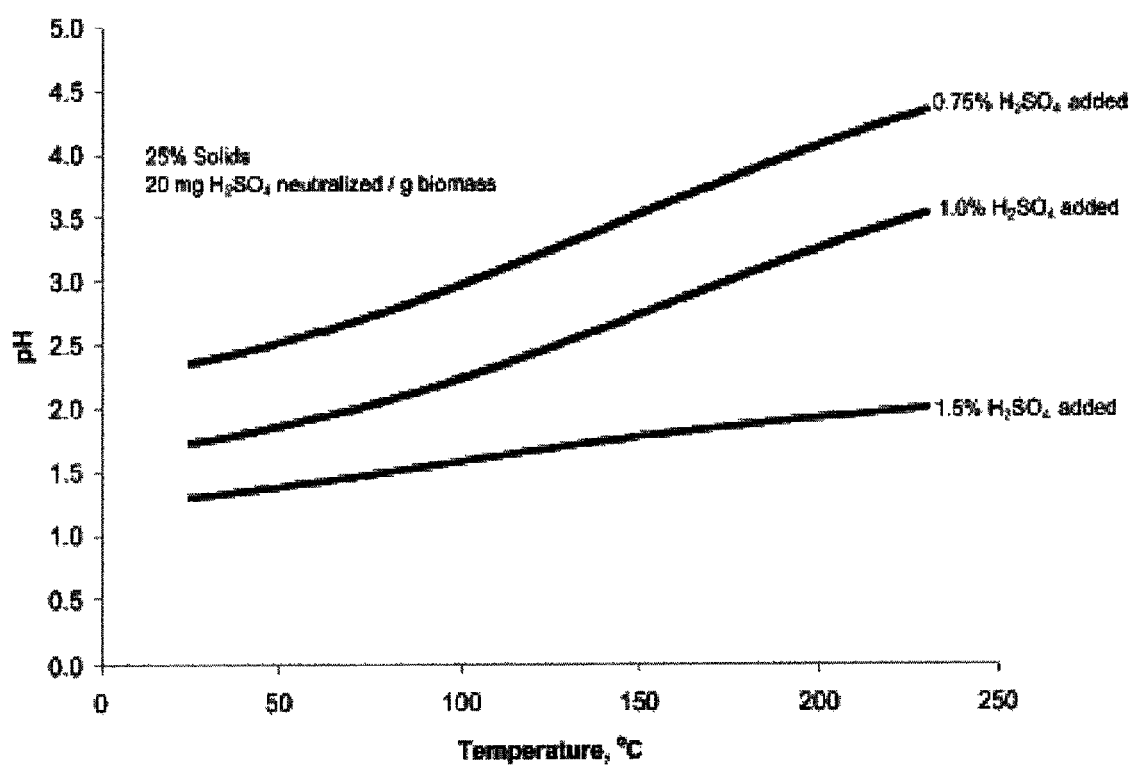
FIG. 4 shows calculated temperature versus pH curves at various sulfuric acid loadings.

FIG. 4 shows the effect of initial acid concentration on 25% solids loading, where 20 mg of sulfuric acid is neutralized per g of dry biomass. As the ratio of neutralization products to sulfuric acid increases, pH becomes increasingly temperature dependent (FIG. 2). As an example, consider a batch pretreatment at 25% solids performed at 160° C. Adding a sulfuric acid solution with an initial concentration of 1.5% (w/w) before 20 mg/g biomass neutralization occurs, and assuming that neutralization products are not removed, the pH shown in FIG. 4 is 1.81. Intuitively, one would expect that cutting the acid concentration in half would also cut the hydrogen ion activity in half, but FIG. 4 shows that a pH of 3.64 would be obtained for an initial sulfuric acid concentration of 0.75% at 160° C., a reduction of greater than 98% rather that the 50% level expected. By contrast, if there had been no neutralization, reducing the acid addition from 1.5 to 0.75% at 160° C. would result in the pH rising from 1.00 to 1.26, corresponding to a 45% reduction in hydrogen ion activity. This is somewhat less than the 50% expected owing to an increase in activity as concentration decreases.

Neutralization of sulfuric acid by minerals in biomass reduces the hydrogen ion activity and must be taken into account to accurately predict the performance of dilute-acid hemicellulose hydrolysis. Furthermore, in the case of sulfuric acid, the neutralization products lead to a bisulfate ion shift, further reducing active hydrogen ion. Neutralization and formation of bisulfate can have particularly significant effects for low acid concentration or high solid loadings. Removal of minerals prior to hydrolysis may reduce acid consumption for hemicellulose hydrolysis while maintaining high sugar yields.

Example 3

Mineral Wash of a Biomass

Mineral washing may, for example, be performed using a dilute acid solution that solubilizes the minerals. In one particular embodiment, a dilute sulfuric acid wash solubilizes minerals in the biomass. Removal of the wash solution eliminates bisulfate, which would, if otherwise left present in the biomass, have a buffering effect and require the addition of significantly more acid for satisfactory acidification results. As shown by way of example in FIG. 6, system modifications may be made to perform this prewashing step prior to any acidification. These instrumentalities permit the use of dilute acid or other mineral-removing washes with special advantage. It will be appreciated that a wide-ranging variety of biomass conversion processes utilize acidification, and all such processes may benefit from the prewashing step to remove minerals as described herein.

Milled cellulosic biomass is contacted by a dilute acid solution by any number of methods at temperatures which neutralize minerals in the biomass but solubilize no carbohydrates. Soluble mineral salts are removed by any number of washing methods before the biomass is advanced to a high temperature acid catalyzed treatment step.

Figure 5:
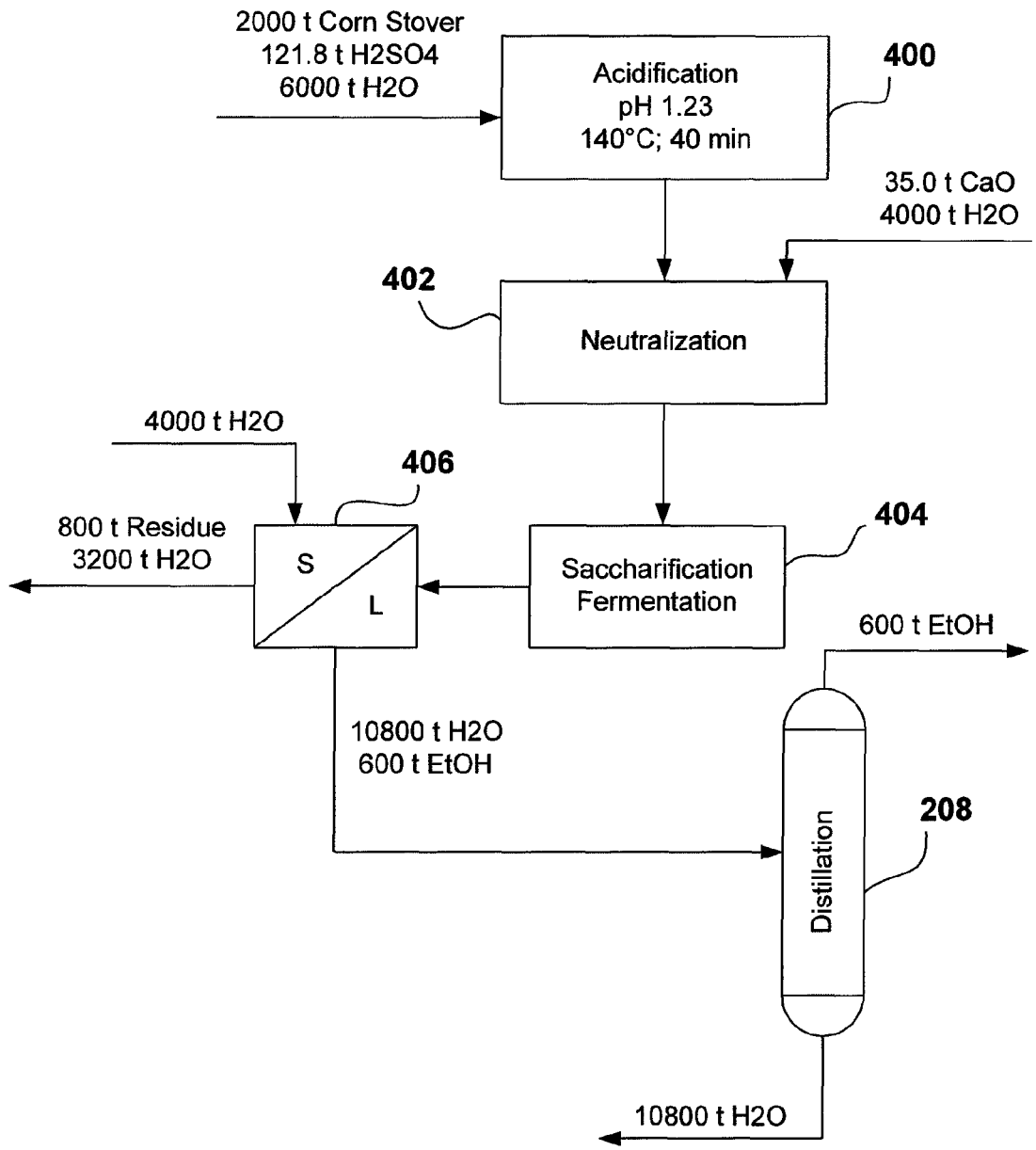
FIG. 5 is a process schematic showing acidification without acid neutralization of minerals.
Figure 6:
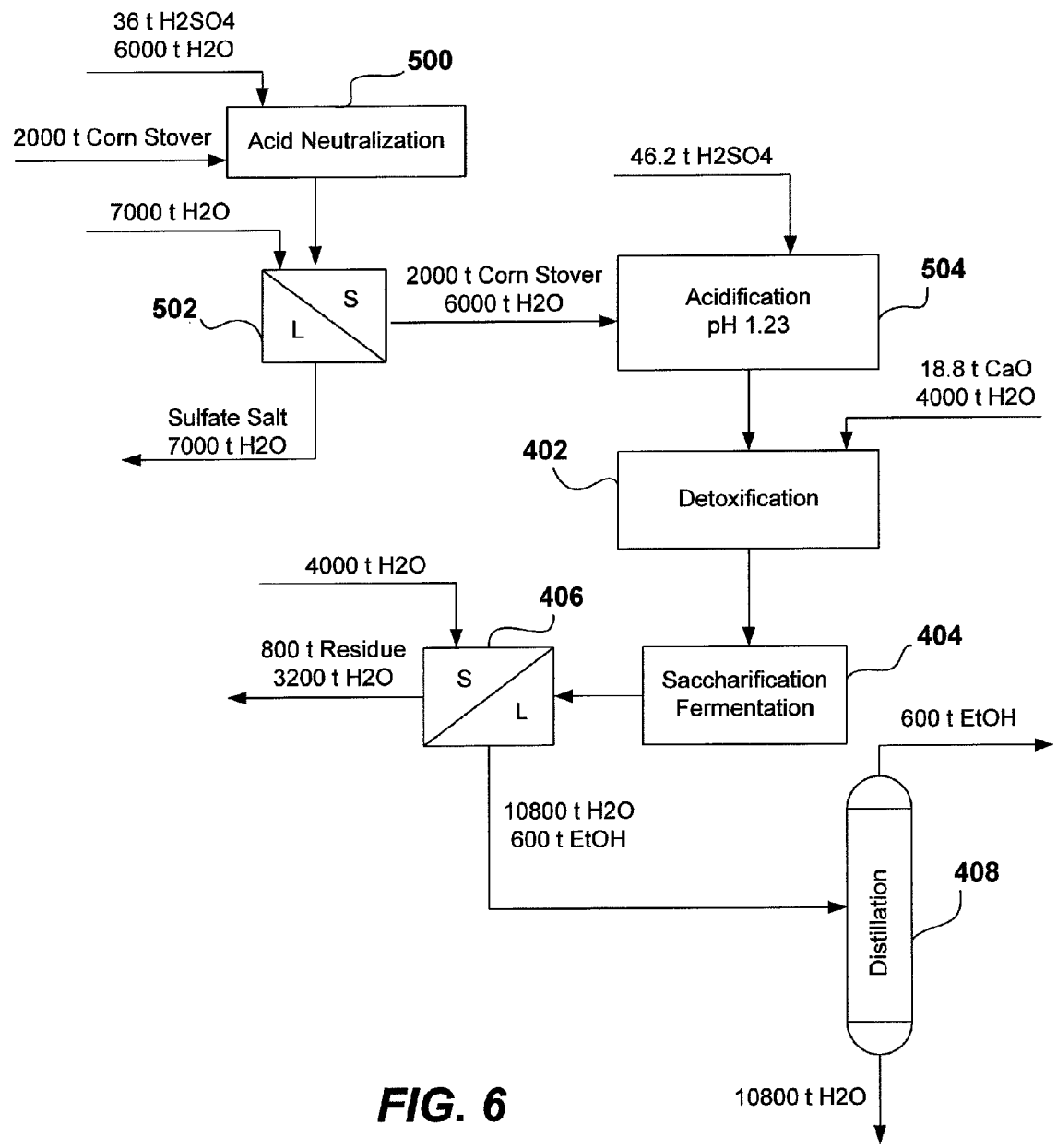
FIG. 6 is a process schematic showing acidification with acid neutralization of minerals.

In one embodiment, the advantage of removing mineral salts prior to a sulfuric acid treatment step is that acid scavenging bisulfate formation is minimized potentially requiring less acid for high overall sugar yields in saccharification, as compared to not removing mineral salts. FIGS. 5 and 6 are process schematics respectively showing the acid that is required without removal of minerals (FIG. 5) and with removal of minerals (FIG. 6). A comparison of these results shows that a ⅓ reduction in acid use is obtainable by removing minerals inherent to the biomass prior to fall acidification.

Neutralization may be achieved over a wide range of biomass moisture contents. At high solids and low moisture it may be possible to add small amounts of concentrated acid directly to biomass in a high solids mixer such as a screw mixer or screw conveyor which provides the requisite contact with the biomass for neutralization. In another example, the biomass may be diluted with acidified water to a solids content that allows tank mixing of a biomass slurry. Either method is feasible and the choice of method may be affected by how much additional water an overall process can economically tolerate.

After neutralization, soluble mineral salts are removed by washing. In a case where the biomass contains a relatively high amount of solids for neutralization, it may be feasible to apply a spray wash using a continuous belt filter. This arrangement may be effective with the addition of a minimal amount of wash water. For the low solids case, a biomass slurry may be applied to a continuous belt filter for dewatering followed by a spray wash to remove residual salts. Any particular mechanical arrangement is suitable if designed for the function of applying the prewash to neutralize or solubilize minerals, which are removed at least in part by removal of the prewash solution precedent to full acidification. The prewash solution may contain, for example, dilute acid such as sulfuric, hydrochloric, nitric and/or organic acid. Surfactants and mineral scavenging materials that react with or adsorb particular minerals may also be useful in the removal of minerals, e.g., ethylenediaminetetraacetic acid (EDTA).

FIG. 5 illustrates the processing of biomass without acid prewash to neutralize minerals in the biomass. Accordingly, by way of illustration, 2000 tons of corn stover are mixed with 121.8 tons of $H_2SO_4$ and 6000 tons of water for acidification in step 400. The solution has a pH of 1.23 and acidification lasts for forty minutes. Acidification is performed primarily for saccharification of hemicellulose and may also have beneficial action against lignin. The acid is neutralized in step 402 by the addition of 35 tons of calcium oxide and 4000 tons of water. Saccharification of cellulose and fermentation of sugars occurs in step 404 for the production of ethanol. A two stage or solid/liquid separator 406 accepts a feed including 4000 tons of additional water. The separator 406 provides a first flow stream including 800 tons of solids and 3200 tons of liquid from the fermenter. A second flow stream contains 10,800 tons of water and about 600 tons of ethanol. A distillation column separates the water from the ethanol. The total amount of $H_2SO_4$ required to produce the 600 tons of ethanol is about 121.8 tons. Process water requirements are 14,000 tons.

FIG. 6 shows the process of FIG. 5 as it may be modified to perform acid neutralization with particular advantage. FIG. 6 retains identical numbering of the same components with respect to FIG. 5. FIG. 6 differs from FIG. 5 by the addition of an acid neutralization step 500. This entails mixing 2000 tons of corn stover with 36 tons of $H_2SO_4$ and 6000 tons of water. Conditions of the acid neutralization step 500 are generally, in a preferred sense, sufficient to remove minerals but not so harsh as to saccharify hemicellulose. Total effluent from the acid neutralization step 500 is applied to a solid/liquid separator 502, which accepts an additional 7000 tons of water. The liquid flow stream from separator 502 contains a sulfate salt and removes bisulfate from the process. The solids flow stream contains 2000 tons of corn stover and 6000 tons of water. This is combined with 46.2 tons of $H_2SO_4$ for performance of the acidification step 504. Notably, the 46.2 tons of $H_2SO_4$ is sufficient to establish the same acidification effects in step 504 as compared to step 400 in FIG. 5, and this is made possible by removal of minerals from the corn stover biomass. The remainder of the process in FIG. 6 proceeds in the same manner as shown by identical numbering with respect to FIG. 5. Advantageously, only 76.2 tons of $H_2SO_4$ are required to produce the 600 tons of ethanol. Process water requirements are increased to 21,000 tons as shown in FIG. 6, but this may be reduced by choice of the separators 502, 406, the use of spray washing as described above, and/or water recycle.

The specific weights shown in FIGS. 5 and 6 are used to show relative amounts of materials that pertain to one type of a corn stover biomass feed. Actual amounts may vary as needed to optimize process results depending upon the biomass source and the mineral content that is inherent to the biomass source. The comparison between FIGS. 5 and 6 merely represents by way of example the general principle of reducing acid consumption by implementing an acid neutralization step through which minerals are removed from the biomass prior to full acidification treatment for saccharification of hemicellulose.

The description of the specific embodiments reveals general concepts that others can modify and/or adapt for various applications or uses that do not depart from the general concepts. Therefore, such adaptations and modifications should and are intended to be comprehended within the meaning and range of equivalents of the disclosed embodiments. It is to be understood that the phraseology or terminology employed herein is for the purpose of description and not limitation.

All references mentioned in this application are incorporated by reference to the same extent as though fully replicated herein.

What is claimed is:

1. A method of evaluating mineral content in a cellulosic biomass, said method comprising:
    (a) pre-washing said biomass with an acid;
    (b) allowing said acid to neutralize one or more minerals present in said biomass; and
    (c) determining the amount of said acid consumed by said mineral neutralization and bisulfate salt formation per mass of said cellulosic biomass.

2. The method of claim 1, wherein said method further comprises a step of determining a pH of a slurry formed by said cellulosic biomass.

3. The method of claim 2, wherein said method further comprises steps of determining a pH of a slurry formed by an ideal cellulosic biomass and comparing said pH of the slurry formed by the ideal cellulosic biomass with the pH obtained in claim 2.

4. The method of claim 1, wherein said method further comprises a step of determining a pH of a slurry formed by said cellulosic biomass as a function of temperature of said slurry.

5. The method of claim 4, wherein said temperature is between 25-200° C.

6. The method of claim 4, wherein said temperature is between 25-85° C.

7. The method of claim 1 further comprising determining a pH of a slurry formed by said cellulosic biomass as a function of solids concentration.

8. The method of claim 7, wherein the solids concentration is between 10% and 35%.

9. The method of claim 1 wherein the one or more minerals are at least one mineral selected from the group consisting of potassium, sodium, calcium and iron.

10. The method of claim 1, wherein the step (c) of determining is performed experimentally.

11. The method of claim 1, wherein the step (c) of determining involves correlation with mineral analyses.

12. The method of claim 1, wherein the cellulosic biomass is selected from the group consisting of wood, corn stover, sawdust, bark, leaves, agricultural and forestry residues, grasses, ruminant digestion products, municipal wastes, paper mill effluent, newspaper, cardboard and combinations thereof.

13. The method of claim 1, wherein the step (c) of determining involves solving:

$$k_h = A_0 \alpha_{H^+} e^{-E/RT} \tag{25}$$

where $k_h$ is a rate of hydrogen ion activity, $A_0$ is a preexponential factor, $a_{H^+}$ is an ionic activity of hydrogen ion, E is activation energy, R is the gas constant, and T is temperature.

14. The method of claim 13, wherein the temperature is between 25° C. and 200° C.

15. The method of claim 13, wherein the temperature is between 25° C. and 85° C.

* * * * *